US00PP12892P2

(12) United States Plant Patent
Nicolle

(10) Patent No.: US PP12,892 P2
(45) Date of Patent: Aug. 27, 2002

(54) PRIMULA PLANT NAMED 'PRINIC'

(75) Inventor: Geoff Nicolle, Haverfordwest (GB)

(73) Assignee: Blooms of Bressingham Ltd., Norfolk (GB)

( * ) Notice: Subject to any disclaimer, the term of this patent is extended or adjusted under 35 U.S.C. 154(b) by 74 days.

(21) Appl. No.: 09/765,456

(22) Filed: Jan. 22, 2001

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Annette Para
(74) *Attorney, Agent, or Firm*—C. A. Whealy

(57) ABSTRACT

A distinct cultivar of Primula plant named 'Prinic', characterized by its fully double flowers that do not produce seed; dark yellow petal coloration; strongly fragrant flowers; and long-lasting flowers.

1 Drawing Sheet

BACKGROUND OF THE INVENTION

The present Invention relates to a new and distinct cultivar of Primula plant, botanically known as *Primula veris*× *Primula polyanthus*, marketed under the trade name Katy McSparron, and hereinafter referred to by the name Prinic.

The new Primula is a product of a planned breeding program conducted by the Inventor in England. The objective of the breeding program is to develop new Primula cultivars with fully double flowers.

The new Primula originated from a cross made by the Inventor of an unnamed selection of *Primula veris*, not patented, as the female, or seed parent, with an unnamed selection of *Primula polyanthus*, not patented, as the male, or pollen, parent. The cultivar Prinic was discovered and selected by the Inventor as a flowering plant within the progeny of the stated cross in a controlled environment in England in 1990.

Asexual reproduction of the new cultivar by divisions taken at Pembrokeshire, Wales, has shown that the unique features of this new Primula are stable and reproduced true to type in successive generations.

SUMMARY OF THE INVENTION

Plants of the cultivar Prinic have not been observed under all possible environmental conditions. The phenotype may vary somewhat with variations in environment such as temperature, light intensity, daylength, fertility level, and/or water status without, however, any variance in genotype.

The following traits have been repeatedly observed and are determined to be the unique characteristics of 'Prinic'. These characteristics in combination distinguish 'Prinic' as a new and distinct cultivar:

1. Fully double flowers that do not produce seed.
2. Dark yellow petal coloration.
3. Strongly fragrant flowers.
4. Long-lasting flowers.

Plants of the new Primula differ from plants of the female parent, the unnamed selection of *Primula veris*, in the following characteristics:

1. Plants of the new Primula have fully double flowers that do not produce seed whereas plants of the female parent have single flowers and produce seed.

2. Plants of the new Primula have a stronger fragrance than plants of the female parent.
3. Plants of the new Primula have longer-lasting flowers than plants of the female parent; flowers of the new Primula last about 20 days longer than flowers of the female parent.

Plants of the new Primula differ from plants of the male parent, the unnamed selection of *Primula polyanthus*, primarily in that plants of the new Primula have fully double flowers that do not produce seed whereas plants of the male parent have hose-in-hose flowers and produce seed.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ from the color values cited in the detailed botanical description which accurately describe the colors of the new Primula. The photogaph comprises a side perspective view of typical plants of 'Prinic' grown in the landscape.

DETAILED BOTANICAL DESCRIPTION

In the following description, color references are made to The Royal Horticultural Society Colour Chart except where general terms of ordinary dictionary significance are used. Plants were grown in Norfolk, England under field conditions which closely approximate commercial production conditions. During the production of the plants, day temperatures ranged from 5 to 28° C. and night temperatures ranged from −8 to 15° C. Plants used for the description were about one year old from planting rooted cuttings.

Botanical classification: *Primula veris*×*Primula polyanthus* cultivar Prinic.

Parentage:

*Female, or seed, parent.*—Unnamed selection of *Primula veris*, not patented.

*Male, or pollen, parent.*—Unnamed selection of *Primula polyanthus*, not patented.

Propagation:

*Type.*—By tissue culture.

*Time to initiate roots on a tissue-cultured mirco-cutting.*—Summer: About 10 days at 20° C. Winter: About 15 days at 10° C.

*Time to produce a rooted liner from a tissue-cultured micro-cutting.*—Summer: About 15 days at 20° C. Winter: About 20 days at 10° C.

*Root description.*—Fibrous and thick.

Plant description:

*Rate of growth.*—During one growing season in England, plants of the new Primula will grow to about 20 cm in height; plants will grow about 3 to 5 cm per subsequent growing season.

*Form.*—Low spreading and clumping perennial; leaves basal.

*Usage.*—Appropriate for five-liter containers.

*Plant height, soil level to top of plant plane.*—About 20 cm.

*Plant width.*—About 30 cm

*Foliage description.*—Leaves simple, generally symmetrical and long persisting. Length, mature leaves: About 15 cm. Width, mature leaves: About 5 cm. Shape: Obovate. Apex: Rounded. Base: Acuminate. Margin: Crenulate. Texture: Smooth; slightly pubescent on both surfaces. Color: Young foliage, upper surface: 191A. Young foliage, lower surface: 191C. Mature foliage, upper surface: 191B; venation, 191C. Mature foliage, lower surface: 191C; venation, 191C. Petiole: Length: About 3 to 8 cm. Diameter: About 5 mm. Color: 191C.

Flower description:

*Flower type and habit.*—Fully double trumpet-shaped flowers arranged in terminal umbels. Flowers last about two months on the plant. Flowers persistent.

*Fragrance.*—Strongly fragrant; typical of Cowslip.

*Natural flowering season.*—Continuously flowering from March to May in the United Kingdom.

*Quantity.*—Freely flowering: about 150 to 200 flowers and flower buds per plant; about 20 to 25 umbels per plant; and about 6 to 10 flowers per umbel.

*Flower diameter.*—About 1 to 1.5 cm.

*Flower depth* (*height*).—About 5 mm.

*Flower buds.*—Length: About 1.5 cm. Diameter: About 8 mm. Shape: Obovate. Color: 191C.

*Petals.*—Arrangement/appearance: Fully double trumpet-shaped flowers with 12 petals; fused. Length: About 6 mm. Width: About 6 mm. Shape: Lobed. Apex: Rounded. Margin: Entire. Texture: Smooth, soft. Color: Upper surface, when opening: 15C. Lower surface, when opening: 15D. Upper surface, opened flower: 15A; fading to 15B with subsequent development Lower surface, opened flower: 15C.

*Calyx.*—Shape: Funnel-shaped; sepals, five, fused. Length: About 5 to 10 mm. Diameter: About 1 cm. Color: Whitish green.

*Peduncle.*—Strength: Stiff. Angle: Erect. Length: About 25 cm. Color: 191C.

*Reproductive organs.*—Flowers are fully double and reproductive organs have not been observed.

*Seed.*—Seed development has not been observed.

Disease resistance: Under commercial production conditions, plants of the new Primula have not been noted to be resistant to pathogens common to Primula.

It is claimed:

1. A new and distinct cultivar of Primula plant named 'Prinic', as illustrated and described.

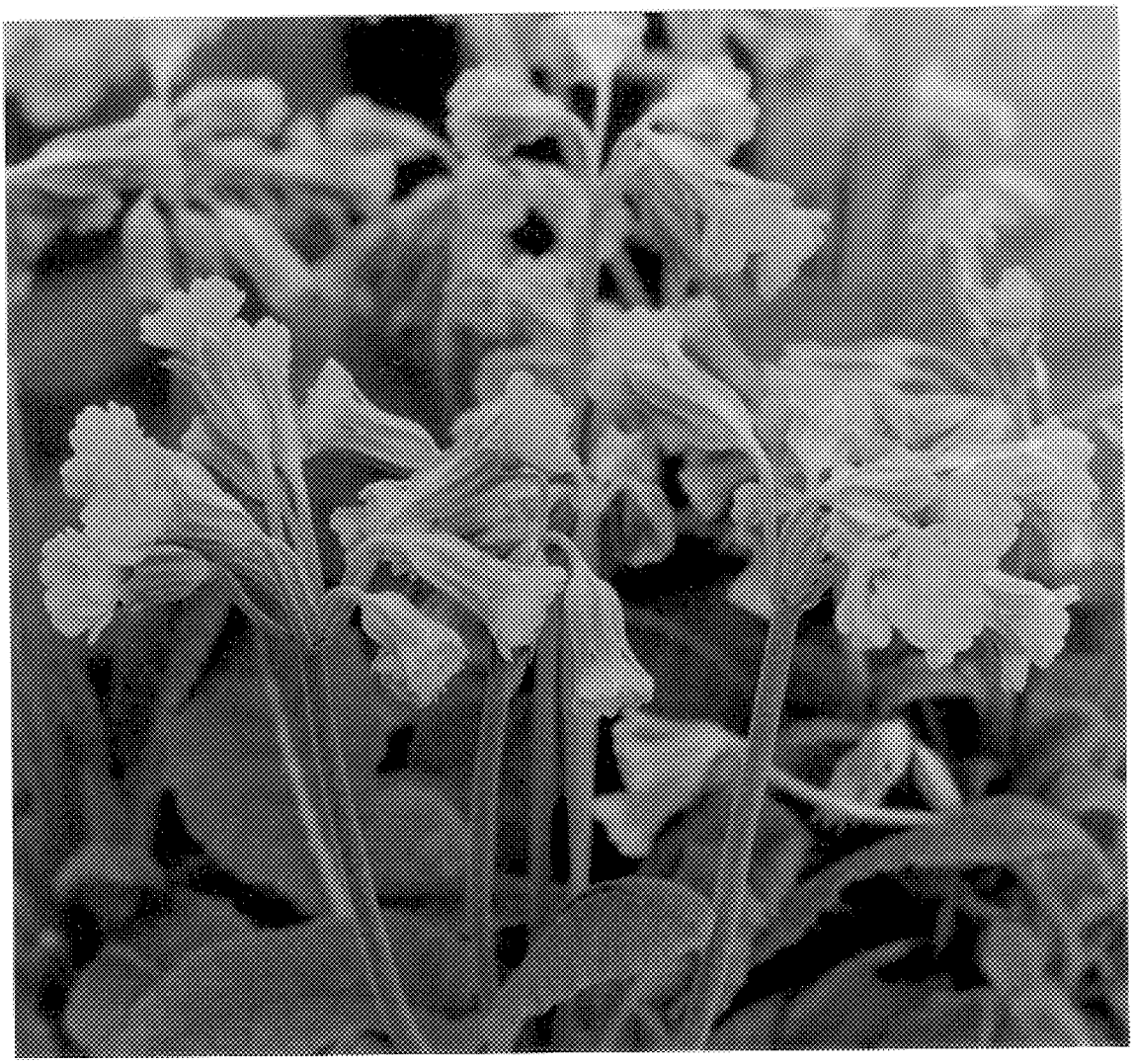

* * * * *